United States Patent [19]
Arlt et al.

[11] Patent Number: 5,656,748
[45] Date of Patent: Aug. 12, 1997

[54] PROCESS FOR THE PREPARATION OF IVERMECTIN

[75] Inventors: Dieter Arlt; Gerhard Bonse, both of Köln; Friedhelm Reisewitz, Wuppertal, all of Germany

[73] Assignee: Bayer Aktiengesellschaft, Leverkusen, Germany

[21] Appl. No.: 606,787

[22] Filed: Feb. 27, 1996

[30] Foreign Application Priority Data

Mar. 1, 1995 [DE] Germany ............ 195 07 018.6

[51] Int. Cl.$^6$ .............. C07H 1/00; C07H 17/08; C07D 311/00; C07D 493/00
[52] U.S. Cl. .............. 536/124; 536/7.1; 549/264
[58] Field of Search ............ 536/7.1, 124; 549/264

[56] References Cited

U.S. PATENT DOCUMENTS 4,873,224  10/1989  Linn et al. .................. 536/7.1

FOREIGN PATENT DOCUMENTS

| 0001689 | 5/1979 | European Pat. Off. . |
| 0187436 | 7/1986 | European Pat. Off. . |
| 0266131 | 5/1988 | European Pat. Off. . |
| 0411854 | 2/1991 | European Pat. Off. . |

*Primary Examiner*—John Kight
*Assistant Examiner*—Everett White
*Attorney, Agent, or Firm*—Sprung Horn Kramer & Woods

[57] ABSTRACT

The invention relates to a process for the selective hydrogenation of avermectins with the aid of a rhodium-phosphine complex based on a hydrazine.

3 Claims, No Drawings

PROCESS FOR THE PREPARATION OF IVERMECTIN

Ivermectin is a known compound which has outstanding biological actions and is widely used as an anthelmintic, ectoparasiticide, insecticide and acaricide.

It is known (EP 0 001 689) to prepare ivermectin from avermectin $B_{1a}$ and $B_{1b}$ by selective catalytic hydrogenation. Avermectin is obtained biotechnologically with the aid of Streptomyces avermitilis. It has five double bonds. In order to prepare ivermectin from this starting material, a selective catalyst which only hydrogenates the 22,23 double bond is required.

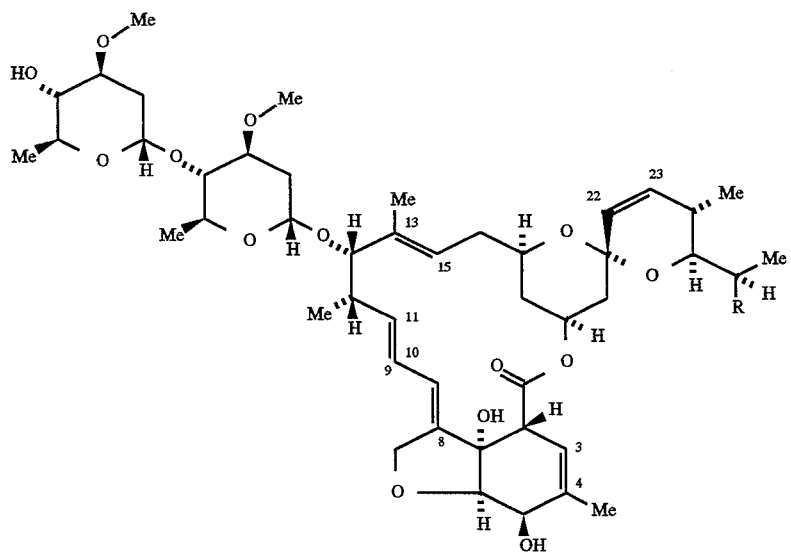

Avermectin $B_{1a}$ (R: -ethyl)
Avermectin $B_{1b}$ (R: -methyl)

It is disclosed in EP 0 001 689 that catalysts of the general formula $[(R)_3P]_3$ RhX can be used for this purpose; preferably the Wilkinson catalyst $[Ph_3P]_3RhCl$ is employed. It is to be inferred from EP 0 001 689 that relatively large amounts of this catalyst (0.05 to 0.5 mol/mol of avermectin) must be used in order to achieve the desired hydrogenation.

Because of the high price of the catalyst, in particular due to the content of expensive rhodium, it was therefore proposed (EP 0 059 616) advantageously to employ a special recovery process for the recovery of the considerable amounts of this noble metal which have to be used for the preparation of ivermectin. The corresponding examples of EP 0 059 616 show that even after years of process development apparently amounts of up to 10% of catalyst based on starting material are still used. The most favourable example of this patent specification in this respect indicates a catalyst charge of >1% based on starting material.

There is accordingly a need to find processes which enable the amount of catalyst, in particular the amount of expensive rhodium, to be decreased markedly compared with the known prior art in the preparation of ivermectin from avermectin $B_{1a}$ and $B_{1b}$ by catalytic hydrogenation.

Surprisingly, it has now been found that when using Rh catalysts which, in addition to phosphines, also contain hydrazines as ligands, the necessary amount employed for the selective hydrogenation of avermectin $B_{1a}$ and $B_{1b}$ can be considerably reduced.

The present invention accordingly relates to a process for the preparation of ivermectin from mixtures of avermectin $B_{1a}$ and $B_{1b}$ by selective catalytic hydrogenation of the 22,23 double bond in the starting material, characterized in that, as catalyst, an Rh complex compound which is obtained by the reaction of a rhodium salt, a hydrazine or hydrazine salt and a tertiary phosphine or a rhodium-phosphine complex with a hydrazine or a hydrazine salt is employed.

Catalysts of this type and their preparation are known; see, for example, EP 0 086 046, EP 0 283 615 and Tetrahedron Vol. 7, No. 19/20, pp. 2087–2089 (1988).

The new process is distinguished in that, in contrast to the known prior art, amounts of catalyst of <1% based on the amount of the starting material employed and in an Rh concentration which is only $\leq \frac{1}{10}$ of the concentration necessary according to the prior art lead effectively to the desired product with high selectivity.

The catalytic hydrogenation of the process according to the invention is carried out in customary solvents, such as, for example, alcohols or aromatic hydrocarbons, if appropriate with addition of aliphatic hydrocarbons, for example in methanol, methanol/cyclohexane mixtures or toluene, which is preferably employed. The temperature during the reaction is, for example, in the range from 60° to 100° C. and the hydrogen pressure is in the range from, for example, 1 to 150 bar. In order to shorten the reaction time, it is expedient to work at elevated pressure, a range from 20 to 100 bar being preferred.

After the hydrogenation, the reaction mixture is worked up in a manner known per se, e.g. according to the process described in EP 0 059 616 or alternatively by adsorption of the rhodium on a reactive resin and subsequent purification of the Rh-free product, e.g. by known crystallization processes.

EXAMPLE 1

A) Catalyst (known):

Rhodium trichloride trihydrate (1.00 g, 3.80 mmol) was dissolved in water (5.0 ml) with heating (70° C.). A solution of triphenylphosphine (1.95 g, 7.43 mmol) in acetone (25.0 ml) was then added under a nitrogen atmosphere in the course of 20 minutes. After 10 minutes, hydrazine hydrate (1.90 ml; 39.09 mmol) was added with stirring and the mixture was heated at reflux temperature for 3 hours, then kept at 45° C. for a further 1 hour. The crystalline solid which had then been precipitated was filtered off under nitrogen and washed with a little acetone and then with diethyl ether. 1.05 g of an orange-coloured solid were obtained.

B) Hydrogenation (new):

The catalyst (10 mg) obtained according to A) was dissolved in toluene (25 ml) and added under argon to the solution of a mixture (1.1 g) of avermectin $B_{1a}$ (96%) and avermectin $B_{1b}$ (4%) and of 100 mg of triphenylphosphine in toluene (25 ml) in a stainless steel autoclave. This starting material was then hydrogenated at 88° C. under a hydrogen pressure of 20 bar with stirring of the solution. After 10 hours, HPLC analysis revealed a content of 86% dihydro-avermectin $B_{1a}$ and of 4 % dihydro-avermectin $B_{1b}$, and also of 3% tetrahydro-avermectin $B_{1a}$.

EXAMPLE 2

The catalyst (15 mg) obtained according to Example 1A) was dissolved in a solution of 8.6 g of avermectin $B_{1a}$ and $B_{1b}$ (content 77.5% and 18.0% respectively) in a mixture of 33.3 ml of methanol and 16.7 ml of cyclohexane and, after addition of 80 mg of triphenylphosphine, the solution was hydrogenated with intensive mixing for 8 hours at a temperature of 88° C. and a hydrogen pressure of 20 bar. The product obtained contained, in addition to 6.2% starting material, 84% of 22,23-dihydro-avermectins.

EXAMPLE 3

A) In situ preparation of the catalyst:

A mixture of 4.45 g of rhodium trichloride trihydrate, 11.33 mg of triphenylphosphine, 22.5 µl of water and 3.0 ml of acetone were heated at 60° C. for 30 minutes, then 10 µl of hydrazine hydrate and a further 3.0 ml of acetone were added. This mixture was heated at 60° C. for a further 20 hours with stirring and reflux cooling.

The mixture obtained according to 3A) was added to a solution of 8.6 g of avermectin $B_{1a}$ and $B_{1b}$ in 50 ml of toluene. The mixture was hydrogenated for 10 hours at a temperature of 87° C. and a hydrogen pressure of 10 bar. A product having a content of 92.3% of 22,23-dihydro-avermectins and 3.6% of tetrahydro-avermectins was obtained (according to HPLC analysis).

We claim:

1. Process for the preparation of 22,23-dihydro-avermectins by selective catalytic hydrogenation of avermectin $B_{1a}$ and/or $B_{1b}$, wherein, as catalyst, an Rh complex compound which is obtained by the reaction of the rhodium salt, a hydrazine or a hydrazine salt and a tertiary phosphine or an Rh-phosphine complex compound with a hydrazine or a hydrazine salt is used.

2. Process according to claim 1, wherein the catalytic hydrogenation is carried out in a temperature range from 60° to 100° C. and an $H_2$ pressure of 1 to 150 bar.

3. Process according to claim 1, wherein the catalytic hydrogenation is carried out in aromatic hydrocarbons as solvents.

* * * * *